United States Patent
Roy et al.

(10) Patent No.: US 9,511,510 B2
(45) Date of Patent: Dec. 6, 2016

(54) METHOD FOR CONTROLLING A WORKABILITY PARAMETER OF A CONCRETE IN A MIXER

(71) Applicant: LAFARGE, Paris (FR)

(72) Inventors: Cedric Roy, Crachier (FR); Helene Lombois-Burger, Lyons (FR); Christian Blachier, Vienne (FR); Cedric Juge, L'isle d'abeau (FR); Fabrice Toussaint, Saint-alban de Roche (FR)

(73) Assignee: LAFARGE, Paris (FR)

( * ) Notice: Subject to any disclaimer, the term of this patent is extended or adjusted under 35 U.S.C. 154(b) by 0 days.

(21) Appl. No.: 14/389,263

(22) PCT Filed: Mar. 29, 2013

(86) PCT No.: PCT/FR2013/050711
§ 371 (c)(1),
(2) Date: Oct. 30, 2013

(87) PCT Pub. No.: WO2013/144528
PCT Pub. Date: Oct. 3, 2013

(65) Prior Publication Data
US 2015/0336290 A1    Nov. 26, 2015

(30) Foreign Application Priority Data

Mar. 30, 2012  (FR) ..................... 12 52938

(51) Int. Cl.
*B28C 7/02*  (2006.01)
*B28C 5/00*  (2006.01)
(Continued)

(52) U.S. Cl.
CPC ............... *B28C 7/02* (2013.01); *B28C 5/006* (2013.01); *G01N 11/14* (2013.01); *G01N 33/383* (2013.01); *G01N 2011/0046* (2013.01)

(58) Field of Classification Search
CPC ... B28C 7/02; B28C 7/026; G01N 2011/0046; G01N 33/383
(Continued)

(56) References Cited

U.S. PATENT DOCUMENTS 5,713,663 A    2/1998  Zandberg et al.
8,818,561 B2 *  8/2014  Koehler ................ G01N 11/00
                                                    700/265

(Continued)

FOREIGN PATENT DOCUMENTS

| FR | 2 604 785 | 4/1988 |
| WO | WO 88/02481 | 4/1988 |
| WO | WO 2011/162878 | 12/2011 |

OTHER PUBLICATIONS

International Search Report issued for International Application No. PCT/FR2013/050711, dated Aug. 21, 2013.

*Primary Examiner* — Tony G Soohoo
*Assistant Examiner* — Elizabeth Insler
(74) *Attorney, Agent, or Firm* — Pillsbury Winthrop Shaw Pittman LLP

(57) ABSTRACT

A method for controlling at least one workability parameter of a concrete contained in the container of a mixer with a non vertical rotational axis, includes making the container turn at least at least two different rotational speeds; determining, for each of the rotational speeds, a rotary drive torque C of the container, a value of shear stress r of the concrete and a speed gradient γ of the concrete according to the following relationships: $\tau=T(\omega)\cdot C$ and $\gamma=G(\omega)$. ω where T and G are predetermined functions; determining a relationship of variation of shear stress τ according to the speed gradient γ by extrapolation and/or approximation from the determined (Continued)

values; and providing an indication of the workability parameter of the concrete based on the relationship variation.

15 Claims, 4 Drawing Sheets

(51) Int. Cl.
    *G01N 11/14*     (2006.01)
    *G01N 33/38*     (2006.01)
    *G01N 11/00*     (2006.01)

(58) Field of Classification Search
    USPC .............................................. 73/54.03, 54.31
    See application file for complete search history.

(56) References Cited

U.S. PATENT DOCUMENTS

2004/0149019 A1*   8/2004   Johnson ................. G01N 11/14
                                                                                                             73/54.28
2011/0029134 A1*   2/2011   Hazrati ................... B28C 7/026
                                                                                                              700/265

* cited by examiner

METHOD FOR CONTROLLING A WORKABILITY PARAMETER OF A CONCRETE IN A MIXER

CROSS-REFERENCE TO RELATED APPLICATIONS

This is the U.S. National Stage of PCT/FR2013/050711, filed Mar. 29, 2013, which in turn claims priority to French Patent Application No. 1252938, filed Mar. 30, 2012, the entire contents of these applications are incorporated herein by reference in their entireties.

FIELD OF THE INVENTION

The present invention relates to a method for controlling at least one workability parameter, for example the slump, slump flow, threshold stress, viscosity or the flow rate of a concrete in the container of a mixer with a non vertical rotational axis.

SUMMARY OF THE INVENTION

A concrete is a mixture of aggregates pressed by a binder and water. The binder may be a hydraulic binder for example cement. Thus, cement concrete is mentioned. The binder may be a hydrocarbon binder, for example, bitumen. Thus, bituminous concrete is mentioned.

When it is produced, the concrete has a more or less fluid consistency, then it hardens until becoming solid. The concrete must hence be put in place before substantial hardening. The workability of concrete corresponds to the easiness with which the concrete can be handled. The workability of a concrete may be characterized by the measurement of rheological parameters such as threshold stress, concrete viscosity or by the measurement of parameters resulting from standard tests achieved on the site of usage of the concrete, such as slump, slump flow or flow rate. By way of example, the slump may be measured according to the test described in the European standard NF EN 12350-2 of December 1999.

The measurement of rheological parameters usually requires specific measurement apparatuses. It may be difficult to achieve these measurements on the site of usage of the concrete. On the contrary, the slump, the slump flow and the flow rate may be easily measured on the site of usage of the concrete.

However, there is a need for being able to measure the workability parameter when the concrete is in a mixer with a non vertical rotational axis and it is hence not possible to directly access the concrete in order to prevent an overly significant drift of the workability parameter. It is the case, for example, when the concrete is in the container of a mixer truck during the transport of the concrete from the concrete manufacturing site to the concrete usage site.

There exist indirect methods for measuring the slump of a concrete in a mixer. By way of example, U.S. Pat. No. 5,713,663 describes an indirect method for measuring the slump of a concrete in the turning container of a mixer truck based on the drive torque applied to the container. The slump may then be adjusted by adding water or adjuvant to the concrete. In the case where the container is driven in rotation by a hydraulic motor, the motor torque may be determined based on the measurement of the pressure of the hydraulic fluid supplied to the motor. The slump is then determined by an empirical formula based on the measured hydraulic pressure.

The method comprises a prior step of determining, for each formulation of concrete liable to be manufactured, the empirical formula representing the variation of the slump of the concrete according to the hydraulic pressure.

An ordinary concrete corresponds to a concrete for which the slump usually ranges between 10 mm and 220 mm measured according to the European standard NF EN 12350-2 of December 1999. The test consists in filling a reference frustum of a cone with the concrete to be tested, freeing the concrete from the frustum of a cone, then determining the height from which the concrete has slumped.

The fluid concrete is a concrete for which the slumping is too high to be measured correctly by the test of the European standard NF EN 12350-2 of December 1999. In this case, it can be measured the slump flow which corresponds to the previous test with the difference that it is the diameter of the concrete disc obtained after removal of the mold which is measured according to European standard NF EN 12350-8 of November 2010. It can also be measured the flow rate according to European standard NF EN 12350-9 of November 2010 by letting the concrete flow into a funnel and by measuring the flow duration of the concrete between two marks of the funnel.

The measuring method described in U.S. Pat. No. 5,713,633 is not suitable for fluid concretes. In fact, for fluid concretes, the slump/slump flow of the concrete hardly varies according to the hydraulic pressure. Hence, it is not possible to obtain a precise measurement of the slump/slump flow of the concrete by measuring the hydraulic pressure according to the method of U.S. Pat. No. 5,713,633.

Another drawback of such a measuring method is that it is necessary to determine the empirical formula representing the variation of the slump of the concrete according to the hydraulic pressure for each formulation of concrete liable to be manufactured. Thereby, the method cannot be implemented when the formulation of concrete is modified. It is thus necessary to determine a new empirical formula for the new formulation.

Another drawback of such a measuring method is that it does not allow measuring workability parameters of the concrete other than the slump, for example the threshold stress or the viscosity of the concrete. However, it may be advantageous to measure such rheological parameters in the case of fluid concretes which are liable to be pumped.

Hence, there is a need for a method for controlling at least one workability parameter, in particular the slump, the slump flow, the threshold stress, the flow rate and/or the viscosity of a concrete in the container of a mixer with a non vertical rotational axis which allows determining with precision this workability parameter even in the case where the fluidity of the concrete is high.

SUMMARY

An object of the present invention is to compensate for all or part of the aforementioned drawbacks.

Another object of the present invention is to propose a method for controlling a workability parameter, in particular the slump, the slump flow, the threshold stress, the flow rate and/or viscosity, of a concrete in the container of a mixer with a non vertical rotational axis which does not depend on the fluidity of the concrete.

Another object of the present invention is that the method may be implemented for new formulations of concrete without requiring additional adaptation operations.

Thus, the present invention provides a method for controlling at least one workability parameter of a concrete contained in the container of a mixer with a non vertical rotational axis, comprising the following steps:

making the container turn at at least two different rotational speeds;

determining, for each of said at least two rotational speeds $\omega$, a rotary drive torque C of the container, a value of shear stress $\tau$ of the concrete and a value of speed gradient $\dot{\gamma}$ of the concrete according to the following relationships:

$$\tau = T(\omega) \cdot C$$

$$\dot{\gamma} = G(\omega) \cdot \omega$$

where T and G are predetermined functions;

determining a relationship of variation of the shear stress $\tau$ according to the speed gradient $\dot{\gamma}$ by extrapolation and/or approximation based on the determined values; and providing an indication of the workability parameter of the concrete based on the relationship of variation.

According to an embodiment example of the invention, the method comprises the following steps:

making the container turn at a first rotational speed and determining a first rotary drive torque of the container at the first rotational speed;

making the container turn at a second rotational speed and determining a second rotary drive torque of the container at the second rotational speed;

determining a first shear stress equal to the product of the first torque and to the value of the function T at the first rotational speed;

determining a first speed gradient equal to the product of the first rotational speed and to the value of the function G at the first rotational speed;

determining a second shear stress equal to the product of the second torque and to the value of the function. T at the second rotational speed;

determining a second speed gradient equal to the product of the second rotational speed and to the value of the function G at the second rotational speed; and determining the relationship of variation of the shear stress according to the speed gradient by extrapolation and/or approximation based on the first and second shear stresses and the first and second speed gradients.

According to an embodiment example of the invention, the method comprises the following steps:

making the container turn at a third rotational speed and determining a third rotary drive torque of the container at the third rotational speed;

determining a third shear stress equal to the product of the third torque and to the value of the function T at the third rotational speed;

determining a third speed gradient equal to the product of the third rotational speed and to the value of the function G at the third rotational speed; and determining the relationship of variation of the shear stress according to the speed gradient by extrapolation and/or approximation in addition based on the third shear stress and the third speed gradient.

According to an embodiment example of the invention, the workability parameter of the concrete is selected from among the slump, the slump flow, the threshold stress, the viscosity and the flow rate.

According to an embodiment example of the invention, the method comprises the determination of the threshold stress of the concrete based on the relationship of variation and the determination of the slump and/or slump flow based on the threshold stress.

According to an embodiment example of the invention, the method comprises the adjusting in the container of the workability parameter of the concrete by introducing a compound into the container.

According to an embodiment example of the invention, the compound comprises water, an adjuvant or a mixture thereof.

According to an embodiment example of the invention, providing the indication of the workability parameter of the concrete includes the display on a display screen of the workability parameter, the printing of the workability parameter onto a support and/or the storage of a datum representing the workability parameter to a memory.

According to an embodiment example of the invention, the container is driven in rotation by a hydraulic motor comprising an inlet for receiving a hydraulic fluid and an outlet for pushing back the hydraulic fluid, the torque being determined based on a first difference of pressures equal to the difference between the hydraulic pressure measured at the inlet of the hydraulic motor and the hydraulic pressure measured at the outlet of the hydraulic motor.

According to an embodiment example of the invention, the first difference of pressures is decreased by a second difference of pressures equal to the difference between the hydraulic pressure at the inlet of the hydraulic motor and the hydraulic pressure at the outlet of the hydraulic pressure in the absence of concrete in the container at the measurement rotational speed.

According to an embodiment example of the invention, the hydraulic pressure measured at the inlet or at the outlet of the hydraulic motor is equal to the average of a number of sampled pressure values, said number being inversely proportional to the rotational speed of the container.

According to an embodiment example of the invention, during the sampling of the pressure values used for obtaining the hydraulic pressure measured at the inlet or at the outlet of the hydraulic motor, the variations of the rotational speed of the container are lower than a threshold.

According to an embodiment example of the invention, the functions G and T are obtained by determining:

for each concrete of a plurality of different concretes, a variation curve of the drive torque of the container containing said concrete according to the rotational speed of the container;

for each concrete of a plurality of different concretes, a variation curve of the shear stress of the concrete according to the speed gradient of the concrete by means of a rheometer; and for each pair of concretes of the plurality of different concretes, a first point of intersection between the variation curves of the drive torque of the container according to the rotational speed of the container for the concretes of the pair and a second point of intersection between the variation curves of the shear stress according to the speed gradient for the concretes of the pair.

According to an embodiment example of the invention, for the first point of intersection and the second point of intersection of each pair of concretes of the plurality of different concretes, it is determined the value $Gi^{CC}$ of the function G and the value $Ti^{CC}$ of the function T according to the following relationships:

$$G_i^{CC} = \frac{\dot{\gamma}_i}{\omega_i}$$

$$T_i^{CC} = \frac{\tau_i}{C_i}$$

where $\dot{\gamma}_i$ is the speed gradient at the second point of intersection, $\tau i$ is the shear stress of the concrete at the second point of intersection, $C_i$ is the drive torque at the first point of intersection and $\omega_i$ is the rotational speed at the first point of intersection.

According to an embodiment example of the invention, for the first point of intersection and the second point of intersection of each pair of concretes of the plurality of different concretes, it is determined the value $Gi^{Alt}$ of the function G and the value $Ti^{Alt}$ of the function T according to the following relationships:

$$G_i^{Alt} = \sqrt{\frac{C_i}{V \cdot \eta_i \cdot \omega_i}}$$

$$T_i^{Alt} = \frac{1}{G_i^{Pow} \cdot V}$$

where V is the volume of concrete in the container, $\eta_i$ is the apparent viscosity of the concrete equal to the ratio of the shear stress of the concrete at the second point of intersection and the speed gradient at the second point of intersection, $C_i$ is the drive torque at the first point of intersection and $\omega_i$ is the rotational speed at the first point of intersection.

The present invention also provides a memory device on which is stored a computer programme for implementing the aforementioned method.

The present invention also provides a device for controlling at least one workability parameter of a concrete, comprising:

a mixer with a non vertical rotational axis comprising a container containing the concrete;

a system for driving in rotation the container adapted for making the container turn at at least two different rotational speeds;

a first sensor for measuring a datum representing the rotary drive torque of the container;

a second sensor for measuring a datum representing the rotational speed of the container; and a processing module connected to the drive system and to the first and second sensors and configured to determine, for each of said at least two rotational speeds ω, a rotary drive torque C of the container, a value of shear stress τ of the concrete and a speed gradient value $\dot{\gamma}$ of the concrete according to the following relationships:

$$\tau = T(\omega) \cdot C$$

$$\dot{\gamma} = G(\omega) \cdot \omega$$

where T and G are predetermined functions;

determine, a relationship of variation of the shear stress τ according to the speed gradient $\dot{\gamma}$ by extrapolation and/or approximation based on the predetermined values; and provide an indication of the workability parameter of the concrete based on the relationship of variation.

BRIEF DESCRIPTION OF THE DRAWINGS

These objects, features and advantages, as well as others will be exposed in detail in the following description of particular embodiment examples made in a non limiting manner in relation to the accompanying figures among which.

For the sake of clarity, same elements have been designated by the same references in the different figures. Furthermore, only the elements necessary for the comprehension of the invention are represented on the figures and are described.

DETAILED DESCRIPTION

In the rest of the description, the expressions viscosity, apparent viscosity and dynamic viscosity are employed interchangeably for designating the ratio of the shear stress and the speed gradient of the concrete.

Figure 1:
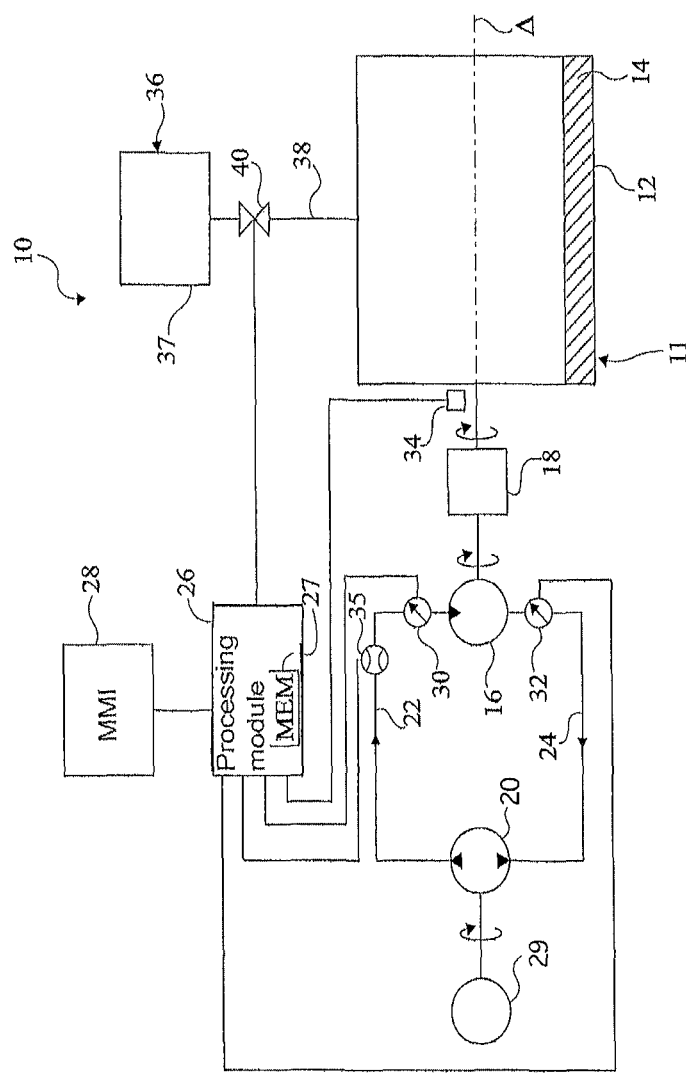
FIG. 1 represents, in a partial and schematic manner, an embodiment example of a device for controlling at least one workability parameter of a concrete in the container of a mixer with a non vertical rotational axis according to an embodiment of the invention.

FIG. 1 represents an embodiment example of a device 10 for controlling at least one workability parameter of a concrete according to an embodiment example of the invention.

A concrete is a mixture of aggregates pressed by a binder and water.

The hydraulic binder is a material which takes and hardens by hydration. Preferably, the hydraulic binder is a cement, in particular a Portland cement, for example a cement of type CEM I, CEM II, CEM III, CEM IV or CEM V according to the European standard NF EN 197-1 of February 2001.

The concrete may be a mixture of a hydraulic binder, aggregates, water, possibly adjuvants, and possibly mineral additions. It consists, for example, of a high performance concrete, of a very high performance concrete, of a self-placing concrete, of a self-leveling concrete, self-compacting concrete, of a fiber-reinforced concrete, of a ready-to-use concrete or of a colored concrete. The term concrete includes mortars. In this case, the concrete comprises a mixture of hydraulic binder, sand, water and possibly additives and possibly mineral additives.

The mineral additives are usually, for example, pozzolanic materials (for example such as defined in the European standard NF EN 197-1 of February 2001 paragraph 5.2.3), silica fume (for example such as defined in the European standard NF EN 197-1 of February 2001 paragraph 5.2.7 or such as defined in the "Concrete" standard prEN 13263: 1998 or NF P 18-502), slags (for example such as defined in the European standard NF EN 197-1 paragraph 5.2.2 or such as defined in the "Concrete" standard NF P 18-506), burnt shale (for example such as defined in the European standard NF EN 197-1 of February 2001 paragraph 5.2.5), materials containing calcium carbonate, for example limestone (for example such as defined in the European standard NF EN 197-1 of February 2001 paragraph 5.2.6 or such as defined in the "Concrete" standard NF P 18-508), siliceous additions (for example such as defined in the "Concrete" standard NF P 18-509), metakaolins and mixtures thereof.

The binder may be a hydrocarbon binder, that is to say, a substance composed of a mixture of hydrocarbons, highly viscous even solid at room temperature. The hydrocarbon binder may, for example, be natural bitumen or raw bitumen a derivative of petrol.

The concrete may be a mixture of a hydrocarbon binder and aggregates, such as for example bituminous concrete, gravel stabilized with bitumen, asphalt, or bituminous emulsion-based surface coatings. A concrete with hydrocarbon binder according to the invention may further comprise usual additives, such as for example adhesion agents or fibers (for example, glass, cellulose or asbestos). A concrete with a hydrocarbon binder may further, comprise recycled materials, such as for example roofing shingles, glass or cement concrete.

The aggregates comprise gravel, coarse aggregates and/or sand. The sand corresponds to a granulate having a granulometry which is strictly lower than 4 mm. The coarse aggregates correspond to aggregates having a granulometry ranging from 4 to 20 mm. The gravel corresponds to aggregates having a granulometry which is strictly higher than 20 mm.

The embodiment examples of the invention are described hereinafter for a concrete comprising a hydraulic binder.

The device 10 comprises a mixer 11 comprising a container 12 in which is disposed a concrete 14. By way of example, the mixer 11 corresponds to a mixer truck used for transporting concrete from a concrete manufacturing site to a concrete usage site. By way of alternative, the mixer 11 may be a stationary mixer with a non vertical rotational axis used for the manufacture of concrete. Preferably, the axis of the mixer is slanted with respect to the horizontal direction of an angle lower than or equal to 45°.

The mixer 11 comprises a hydraulic motor 16 which drives in rotation the container 12 around a non vertical axis $\Delta$ by means of a reducer 18. In the case of a container 12 of a mixer truck, the axis $\Delta$ may be slightly slanted with respect to the horizontal direction. By way of example, the volume V of the concrete 14 in the container 12 may vary from 0.5 $m^3$ to 8 $m^3$, in certain cases, up to 15 $m^3$.

The rotational speed of the container 12 around the axis $\Delta$ may be expressed in radians per second and is thus marked $\omega$ in the rest of the description or is expressed in revolutions per minute and is thus marked N in the rest of the description. By way of example, in the case of a mixer truck, the speed of revolution N may vary from 1 RPM to 20 RPM. By way of example, for transporting concrete, the speed of revolution of the container 12 usually varies from 1 RPM to 6 RPM. For an operation of concrete mixing during the manufacture of the concrete or before the usage of the concrete on the site of usage of the concrete, the rotational speed of the container 12 is usually higher than 6 RPM, and may reach 15 RPM.

The actuation of the hydraulic motor 16 may be achieved by the putting in circulation of a hydraulic fluid by a hydraulic pump 20 connected to the hydraulic motor 16 by a duct 22 for supplying the hydraulic fluid from the hydraulic pump 20 to the hydraulic motor 16 and by a duct 24 for returning the hydraulic fluid from the hydraulic motor 16 to the hydraulic pump 20. The hydraulic pump 20 may be driven in rotation by a motor 29, for example the motor of the mixer truck.

The device 10 comprises a processing module 26, comprising, for example, a microcontroller, comprising a memory (MEM) 27. The processing module 26 is connected to a man/machine interface 28 (MMI) comprising, for example, a display screen, a touch screen, a keyboard, etc.

The device 10 comprises a first hydraulic pressure sensor 30 suitable for measuring the pressure of the hydraulic fluid upstream of the hydraulic motor 16. The device 10 comprises a second hydraulic pressure sensor 32 suitable for measuring the pressure of the hydraulic fluid downstream of the hydraulic motor 16. The sensors 30 and 32 are connected to the processing module 26. One alternative may be to use a differential pressure sensor connected to the inlet and to the outlet of the hydraulic motor 16.

The device 10 may further comprise, a speed sensor 34, connected to the processing module 26, measuring the rotational speed of the container 12. It may consist of a passive rotational speed sensor, in particular, of inductive type, or an active rotational speed sensor, in particular, of magnetoresistive or of Hall effect type. The device 10 may comprise a sensor 35 suitable for measuring the output of the hydraulic fluid circulating in the ducts 22 and/or 24, preferably in duct 22 in the inlet of the hydraulic motor 16.

The device 10 comprises a system 36 for adding water, adjuvant or a mixture of adjuvants in the concrete 14. The adjuvant or the mixture of adjuvants may be added to the water. The system 36 may comprise a tank 37 containing the water, the adjuvant or the mixture of adjuvants. The tank 37 is connected to the container 12 by a duct 38 provided with a valve 40. The valve 40 may be controlled by the processing module 26. By way of example, it may consist of a compressed air valve, the actuation of the valve 40 being obtained by making the compressed air circulate under the control of the processing module 26. By way of alternative, the system 36 may comprise a pump, not represented, connected to the tank 37.

The adjuvants may correspond to adjuvants added in a usual manner in the concretes, in particular a water reducing plasticizer, a superplasticizer, a retarding agent, a setting agent, a thickening agent or a viscosity modifying agent.

Advantageously, the device 10 allows determining the final composition of the concrete, just before the on site usage thereof, with the different additions (in particular, water, the adjuvant or the mixture of adjuvants) and possibly the edition of this updated composition upon reception of the concrete by the client on the site of usage of the concrete.

Figure 2:
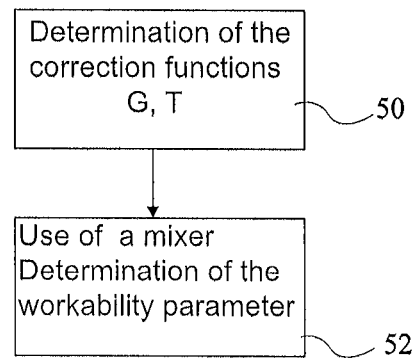
FIG. 2 represents, in the form of a block diagram, an embodiment example according to the invention of a method for controlling a workability parameter of a concrete.

FIG. 2 represents, in the form of a block diagram, an embodiment example according to the invention of a method for controlling at least one workability parameter of a concrete. The method comprises two steps 50 and 52. The step 50 is to be achieved once prior to the anticipated usage of the mixer 11. The step 52 may be implemented at each usage of the mixer 11. The step 52 may be repeated several times during the usage of the mixer 11.

The step 50 comprises the determination of the correction functions G and T and the step 52 comprises the determination (and possibly the adjustment) of a workability parameter based on the correction functions G and T.

The workability parameter may correspond to the slump, the slump flow, to the threshold stress, to the flow rate or to the viscosity of a concrete.

The threshold stress of a concrete is the stress beyond which the concrete starts to flow. When the shear stress $\tau$ is expressed according to the speed gradient $\dot{\gamma}$ (or shear rate), the threshold stress $\tau_0$ corresponds to the shear stress for a speed gradient extrapolated to zero. The apparent viscosity $\eta$ of a concrete corresponds to the ratio of the shear stress $\tau$ and the speed gradient $\dot{\gamma}$. It is not always constant for a concrete but, in certain cases, it may be constant.

Usually, the concrete present in the container 12 may be considered as a Herschel-Bulkley fluid. The expression of the shear stress $\tau$ according to the speed gradient $\dot{\gamma}$ is given by the following function (1):

$$\tau = \tau_0 + k \cdot \dot{\gamma}^p \quad (1)$$

where k and p are positive real numbers. For certain types of concrete, in particular the standard concretes, the concrete may be considered as a Bingham fluid. The expression (1) is thus simplified in the following manner:

$$\tau = \tau_0 + \eta_p \cdot \dot{\gamma} \quad (2)$$

Where $n_p$ is the plastic viscosity of the concrete.

The correction function G is a function which allows obtaining the speed gradient $\dot{\gamma}$ based on the rotational speed $\omega$ of the container 12 according to the following relationship (3):

$$\dot{\gamma} = G(\omega) \cdot \omega \quad (3)$$

The correction function T is a function which allows determining the shear stress $\tau$ based on the rotary drive torque C of the container 12 according to the following relationships (4):

$$\tau = T(\omega) \cdot C \quad (4)$$

The correction functions G and T are functions which are not constant and may depend, in particular on the rotational speed $\omega$. Preferably, the correction functions G and T only depend on the rotational speed $\omega$.

By way of example, the correction functions G and T may be expressed in the form of polynomials according to the following relationships (5) and (6):

$$G = \sum_{j=0}^{M} G_j \omega^j \quad (5)$$

$$T = \sum_{j=0}^{M} T_j \omega^j \quad (6)$$

where $G_j$ and $T_j$ are real numbers and M is an integer higher than or equal to 1.

The correction functions G and T depend on features of the mixer 11 but are independent from formulations of concrete liable to be disposed in the container 12 of the mixer 11.

The method for determining the correction functions G and T is based on the following principle: two concretes for which it is measured the same shear stress $\tau_i$ for a given shear gradient $\dot{\gamma}_i$ develop, in the mixer 11, the same drive torque $C_i$ of the container 12 of the mixer 11 for a given rotational speed $\omega_i$ of the container 12.

Figure 3:
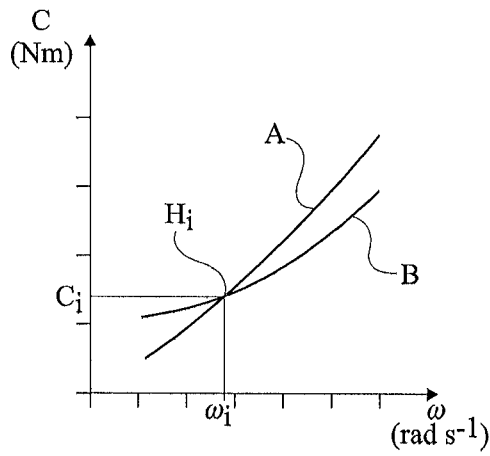
FIG. 3 represents an example of the variation of the torque driving in rotation the container of a mixer with a non vertical rotational axis according to the rotational speed of the container for two concretes of different formulations.
Figure 4:
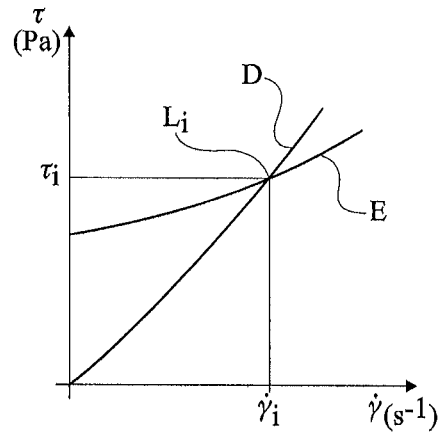
FIG. 4 represents an example of variation of the shear stress τ according to the speed gradient $\dot{\gamma}$ for these two concretes, measured by a rheometer.

FIG. 3 represents the variation curves A and B of the drive torque C of the container 12 according to the rotational speed $\omega$ of the container 12 for two concrete of different formulations and the FIG. 4 represents the variation curves D and E of the shear stress T based on the speed gradient $\dot{\gamma}$ for these two concretes. The curves A and B are determined by using the mixer 11. The curves D and E are determined by using a rheometer.

Curves A and B intersect at a point $H_i$. Curves D and E intersect at a point $L_i$. At point $H_i$, the two concretes have, in the container 12, the same torque $C_i$ at the rotational speed $\omega_i$. At point $L_i$, the two concretes have the same shear stress $L_i$ at speed gradient $\dot{\gamma}_i$. Hence, the two concretes are in the same rheological state at point $L_i$ and at point $H_i$, i.e. they develop the same stress $\tau_i$ for the speed gradient $\dot{\gamma}_i$.

According to an embodiment example according to the invention, the method for determining expressions of the correction functions G and T according to the rotational speed $\omega$ consists in determining the variation curves of the drive torque C according to the rotational speed $\omega$ and the variation curves of the shear stress t according to the speed gradient $\dot{\gamma}$ for several concretes in such a manner as to obtain several intersecting points $H_i$ and $L_i$.

Figure 5:
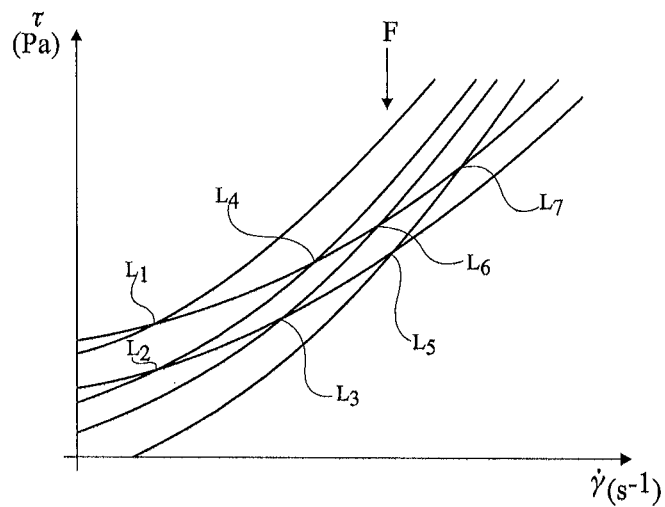
FIG. 5 represents variation curves of the shear stress t according to the speed gradient $\dot{\gamma}$ of concretes of different formulations, measured by a rheometer.

FIG. 5 represents, by way of example, several variation curves F of the shear stress t according to the speed gradient $\dot{\gamma}$ for six concretes of different formulations. These curves intersect at points of intersection $L_1$ to $L_7$.

According to a first example of method for determining expressions of correction functions G and T, for each point of intersection $H_i$ between two variation curves of the drive torque C according to the rotational speed $\omega$ of a pair of concretes and for the point of intersection $L_i$ between the variation curves of the shear stress $\tau$ according to the speed gradient $\dot{\gamma}$ for the same pair of concretes, it is determined the value $G_i^{CC}$ of the correction function G and the value $T_i^{CC}$ of the correction function T according to the following relationships (7) and (8):

$$G_i^{CC} = \frac{\dot{\gamma}_i}{\omega_i} \quad (7)$$

$$T_i^{CC} = \frac{\tau_i}{C_i} \quad (8)$$

The determination of the drive torque is made explicit in further detail hereinafter.

The correction functions G and T may be sought, by way of example, in the form of the aforementioned expressions (5) and (6) by determining parameters $G_j$ and $T_j$ for which the curves of the correction functions G and T pass by values $Gi^{CC}$ and $Ti^{CC}$ or get as close as possible to these vales according to interpolation or approximation methods. Once they are determined, the correction functions G and T are stored in the processing module 26 memory 27.

According to a second example of the method for determining the correction functions G and T, the correction functions G and T are determined based on values $Gi^{Alt}$ and $Ti^{ALT}$ at the points of intersection of index i. The value $Gi^{ALT}$ of the correction function G and the value $Ti^{ALT}$ of the relationship T at the points of intersection of index i are obtained by the following relationships (9) and (10):

$$G_i^{Alt} = \sqrt{\frac{C_i}{V \cdot \eta_i \cdot \omega_i}} \quad (9)$$

$$T_i^{Alt} = \frac{1}{G_i^{Alt} \cdot V} \quad (10)$$

where V is the volume of the concrete 14 in the container 12 and $\eta_i$ is the apparent viscosity of the concrete at the junction point $L_i$.

The correction functions G and T may thus be sought, by way of example, in the form of the aforementioned expressions (5) and (6) by determining the parameters $G_j$ and $T_j$ for which the curves of the correction functions G and T pass by values $Gi^{ALT}$ and $Ti^{ALT}$ or come as close as possible to these values according to the methods of interpolation or approximation. The second example of the method for determining the correction functions T and G has the advantage of being less sensitive to measurement uncertainties than the first example.

Figure 6:
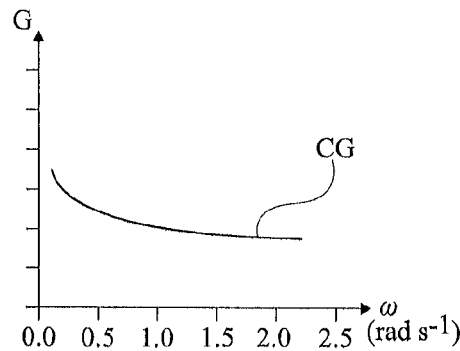
FIG. 6 represents an example of variation curve of the correction function G.
Figure 7:
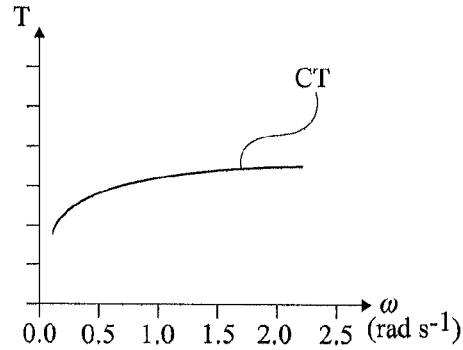
FIG. 7 represents an example of variation curve of the correction function T.

FIGS. 6 and 7 represent two examples of variation curves CG and CT respectively correction functions G and T.

Figure 8:
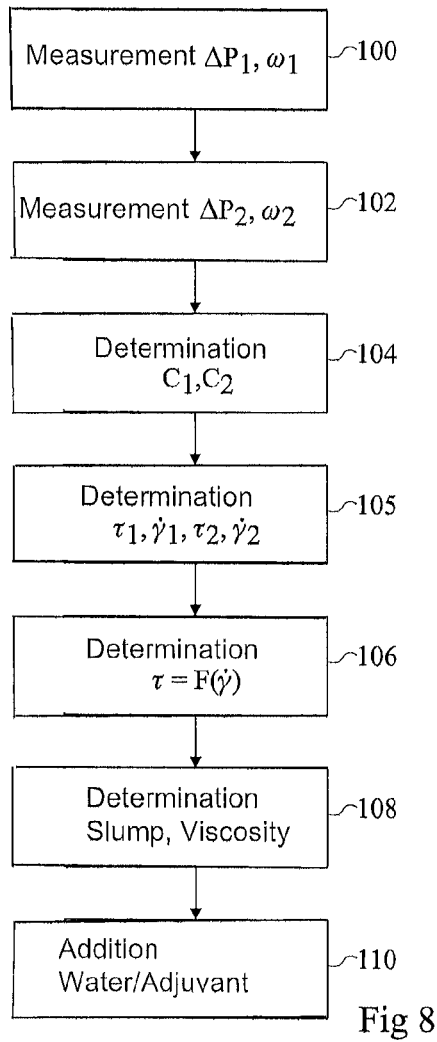
FIG. 8 represents, in the form of a block diagram, a more detailed embodiment example according to the invention of a method for controlling a workability parameter of a concrete.

FIG. 8 represents, in the form of a block diagram, a more detailed embodiment example according to the invention of step 52 of the method, illustrated on FIG. 2.

At step 100, the mixer 11 is controlled at a first operating regime. The processing module 26 determines a first value $\Delta P_1$ from the difference in pressure $\Delta P$ of the hydraulic fluid between the upstream and the downstream of the hydraulic motor 16 and a first value $\omega 1$ of the rotational speed $\omega$ of the container 12. The difference in pressure $\Delta P$ of the hydraulic fluid between the upstream and downstream of the hydraulic motor 16 may be measured by the pressure sensors 30 and 32. The rotational speed $\omega$ of the container 12 may be determined directly by the sensor 34 or indirectly based on the measurement of the flow of hydraulic liquid crossing the hydraulic motor 16. The method continues in step 102.

At step 102, the mixer 11 is controlled at a second operating regime, different from the first operating regime. This means that the rotational speed of the container 12 at the first operating regime 12 is different from the rotational speed of the container 12 at the second operating regime. The processing module 26 thus determines a second value $\Delta P_2$ from the difference in pressure $\Delta P$ of the hydraulic fluid between the upstream and the downstream of the hydraulic motor 16 and a second value $\omega 2$ of the rotational speed $\omega$. The steps 100 and 102 may be repeated several times for other operating regimes of the mixer 11. Preferably, the mixer 11 may, further, be controlled at a third operating regime, different from the first and second operating regimes. The processing module 26 thus determines a third value $\Delta P_3$ from the difference in pressure $\Delta P$ of the hydraulic fluid between the upstream and the downstream of the hydraulic motor 16 and a third value $\omega 3$ of the rotational speed $\omega$. The method then continues at step 104.

Steps 100 and 102 may be implemented automatically or by a voluntary action of the driver of the mixer truck. They can be implemented during the transport of the concrete and/or preferably when the mixer truck is at a standstill.

At step 104, the processing module 26 determines values $C_1$ and $C_2$ of the torque C driving the container 12 respectively based on values $\Delta P_1$ and $\Delta P_2$ from the difference in pressure $\Delta P$ as will be described in further detail herebelow. The method continues at step 105.

At step 105, the processing module 26 determines a first value $\tau 1$ of the shear stress $\tau$ and a first value $\dot{\gamma}_1$ of the speed gradient (or the shear rate) $\dot{\gamma}$ of the concrete at the first operating regime based on values $\Delta P_1$ and $\omega_1$ according to the following relationships (11) and (12):

$$\dot{\gamma}_1 = G(\omega_1) \cdot \omega_1 \quad (11)$$

$$\tau_1 = T(\omega_1) \cdot C_1 \quad (12)$$

Where $G(\omega 1)$ is the value of the correction function G at the rotational speed $\omega 1$ and $T(\omega 1)$ is the value of the correction function T at the rotational speed $\omega 1$.

The processing module 26 further determines, a second value $\tau 2$ of the shear stress $\tau$ and a second value $\dot{\gamma}_2$ of the speed gradient (or shear rate) $\dot{\gamma}$ of the concrete at the second operating regime based on values $\Delta P_2$ and $\omega 2$ according to the following relationships (13) and (14):

$$\dot{\gamma}_2 = G(\omega_2) \cdot \omega_2 \quad (13)$$

$$\tau_2 = T(\omega_2) \cdot C_2 \quad (14)$$

where $G(\omega 2)$ is the value of the correction function G at the rotational speed $\omega 2$ and $T(\omega 2)$ is the value of the correction function T at the rotational speed $\omega 2$.

Preferably, the processing module 26 may further, determine a third value $\tau 3$ of the shear stress $\tau$ and a third value $\dot{\gamma}_3$ of the speed gradient (or shear rate) $\dot{\gamma}$ of the concrete at the third operating regime based on values $\Delta P_3$ and $\omega_3$ according to the following relationships (15) and (16):

$$\dot{\gamma}_3 = G(\omega_3) \cdot \omega_3 \quad (15)$$

$$\tau_3 = T(\omega_3) \cdot C_3 \quad (16)$$

where $G(\omega 3)$ is the value of the correction function G at the rotational speed $\omega 3$ and $T(\omega 3)$ is the value of the correction function T at the rotational speed $\omega 3$.

According to an alternative, the processing module 26 may further, determine other additional values of the shear stress $\tau$ and the shear gradient $\dot{\gamma}$, in addition to the first, second and third aforementioned values.

The method continues at step 106.

At step 106, the processing module 26 determines the expression of the shear stress $\tau$ according to the speed gradient $\dot{\gamma}$ based on the pairs of values $(\tau 1, \dot{\gamma}_1)$ and $(\tau 2, \dot{\gamma}2)$ (and, preferably, in addition, the pair of values $(\tau 3, \dot{\gamma}3)$. At step 106, the processing module 26 may seek the expression $\tau$ in the form of expressions (1) or (2) by determining the parameters $\tau_0$, k and p (or $\eta_p$) for which the variation curve of the shear stress $\tau$ according to the speed gradient $\dot{\gamma}$ passes by the points $(\tau_1, \dot{\gamma}_1)$ and $(\tau_2, \dot{\gamma}_2)$ (and, preferably, in addition to the point $(\tau_3, \dot{\gamma}_3)$) or gets as close as possible to these values according to methods of interpolation or approximation. The method continues at step 108.

At step 108, the processing module 26 determines the workability parameter or the required workability parameters based on the previous expression. The threshold stress $\tau_0$ may be determined directly based on the relationship (1) or (2). The slump or slump flow of the concrete may be determined based on the threshold stress $\tau_0$. By way of example, the slump or slump flow may be obtained according to the following relationships (17) and (18):

$$\tau_0 = E_0 + E_1 \cdot \text{Slump}^\alpha \quad (17)$$

$$\frac{\tau_0}{\rho} = E_2 + E_3 \cdot \text{Slump}^\alpha \quad (18)$$

where E0, E1, E2, E3, and $\alpha$ are real numbers determined beforehand and which are independent from the mixer 11 and the formulation of the concrete and where ρ is the density of the concrete. The apparent viscosity η of the concrete corresponds to the ratio of the shear stress τ and the speed gradient γ̇. The processing module 26 may further, control the interface 28 in order to display the measured workability parameter or workability parameters. Furthermore, the measured workability parameter or workability parameters and the measuring instant may be memorized. The method continues at step 110.

At step 110, the processing module 26 may control the addition in the concrete of water or adjuvants for modifying the measured workability parameter or workability parameters. The step 110 may not be present.

In the embodiment example of the method according to the invention described in relation to FIG. 8, at steps 100 and 102, the pressures are determined based on pressure sensors 30 and 32.

Figure 9:
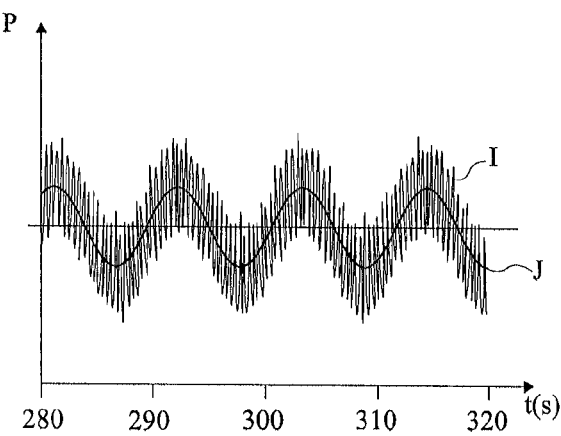
FIG. 9 represents an example of variation of the hydraulic pressure measured at the inlet of the hydraulic motor or of the pressure differential between the inlet and the outlet of the hydraulic motor driving the container of the mixer in rotation.

FIG. 9 represents an example of variation curve I of the signal provided by the sensor 30 for several rotations of the container 12. The curve J represents the variation of the signal provided by the sensor 30 after a low-pass filtering operation. The curve J may comprise oscillations during a revolution of the container 12 which may be in particular due to balancing defects of the container 12, to the nature of the concrete, etc. The frequency of the oscillations substantially corresponds to the frequency of rotation of the container 12. At aforementioned steps 100 and 102, the measured pressure corresponds to an average pressure. It is advantageous, in order to determine average pressure, to take into consideration at least a complete revolution of the container 12. This is why the frame number of successive samples used for determining the average pressure varies according to the rotational speed ω of the container 12. The frame number of samples depends on the number of oscillations $Nb_{osci}$ of the curve during a revolution of the container 12, on the rotational speed N of the container 12 and the frequency f of acquisition of the pressure samples according to the following relationship (19):

$$\text{Frame} = 60 \frac{Nb_{osc} \cdot f}{N} \quad (19)$$

The samples are considered as stable when, for each measured sample from among the Frame number of samples, the rotational speed N of the container 12 hardly varies with respect to an average rotational speed for the Frame number of samples, for example varies by less than 1 revolution per minute with respect to the average rotational speed for the Frame number of samples. The average pressure is only measured when the samples are stable.

The signal provided by the sensor 30 is marked $P_e$ and the signal output from the hydraulic motor 16 obtained based on the sensor 32 is marked $P_s$. The differential pressure ΔP is equal to the difference between the input $P_e$ and output $P_s$ pressures. The average value of the differential pressure is obtained by calculating the average of the values of the differential pressure ΔP of the set of samples from the Frame number of samples.

The relationship between the differential pressure ΔP and the drive torque C is obtained in the following manner. The mechanical power $P_M$ used for the rotation of the revolving drum is given by the following relationship (20):

$$P_M = C \cdot \omega \quad (20)$$

When the hydraulic motor 16 operates in a linear operating range, the mechanical power $P_{hy}$ of the hydraulic motor 16 is given by the following relationship (21):

$$P_{hy} = \Delta P \cdot Q \quad (21)$$

where Q is the output of hydraulic fluid, expressed in m³/s, driving the hydraulic motor 16. The output Q is given by the following relationship (22):

$$Q = C_y \cdot n_m \quad (22)$$

Where $n_m$ is the rotational speed of the hydraulic motor 16 expressed in revolutions per second and $C_y$ is the cubic inch displacement of the hydraulic motor 16. The cubic inch displacement $C_y$, expressed in m³/R, corresponds to the volume of hydraulic fluid which transits in the hydraulic motor 16 during a revolution of the hydraulic motor 16.

Considering that the mechanical power $P_M$ is equal to the product of the hydraulic power $P_{hy}$ and an efficiency factor R and that the rotational speed $n_m$ of the hydraulic motor 16 is equal to the product of the rotational speed ω of the container 12 and a reduction factor $K_r$, the following relationship (23) is obtained:

$$C = R \cdot \Delta P \cdot C_y \cdot K_r \quad (23)$$

The drive torque C may be determined by replacing in the expression (23) the difference in pressure ΔP by the input pressure $P_e$. However, the inventors have emphasized that the precision of the determination of the drive torque C is increased by using the difference in pressure ΔP rather than only the input pressure $P_e$.

The drive torque C which is sought to be measured must represent as much as possible the behavior of the concrete and not other parameters such as for example the friction between the container 12 and the container 12 supporting system or the no load operation container 12 mass.

It may be hence advantageous to measure the variation curve of the input pressure $P_{e0}$ and the variation curve of the outlet pressure $P_{s0}$ according to the rotational speed ω of the container 12 in the absence of the concrete in the container 12 and to subtract the value $P_{e0}$ from the rotational speed of the measurement of the measured pressure $P_e$ and the value Ps0 from the rotational speed of the measurement of the measured pressure $P_s$ during the determination of ΔP.

By naming $\Delta P_0$ the difference of no load operation pressure, i.e. the difference between $P_{e0}$ and $P_{s0}$, the following relationship (24) may thus be used instead of the previous relationship (23):

$$C = R \cdot (\Delta P - \Delta P_0) \cdot C_y \cdot K_r \quad (24)$$

The inventors have, further, emphasized that the precision of the determination of the drive torque C is increased by using the corrected differential pressure $\Delta P - \Delta P_0$ rather than the differential pressure ΔP alone.

The rotational speed ω of the container 12 may be determined directly based on the rotational speed sensor 34 or may be determined indirectly based on the output of the oil Q measured by the sensor 35 according to the following relationship (25):

$$\omega = \frac{Q}{K_r \cdot C_y} \quad (25)$$

Figure 10:
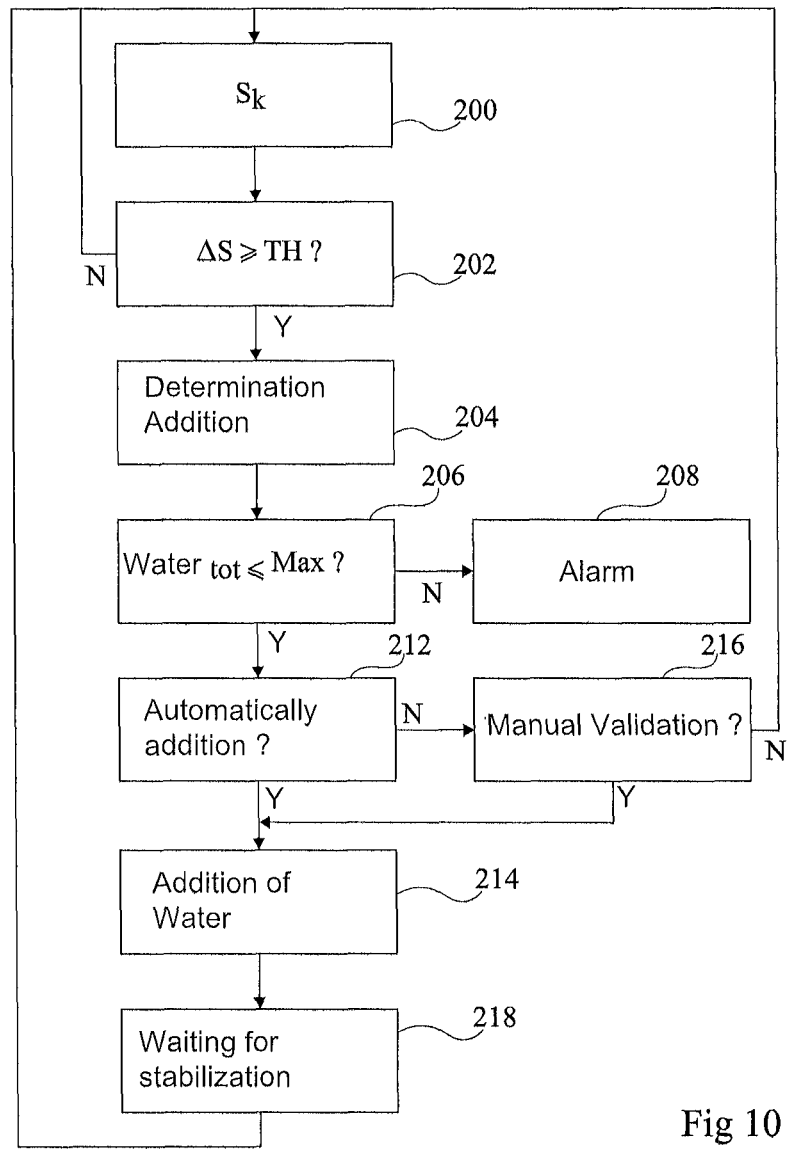
FIG. 10 represents, in the form of a block diagram, an embodiment example of a method for adjusting the slump of a concrete according to the invention.

FIG. 10 represents, in the form of a block diagram, an embodiment example of the step 110 of the method illustrated on FIG. 8 in the case where, at step 108, the method provides a slump value and in the case where the slump is adjusted by adding water to the concrete. This method of adjustment may also be employed for controlling the slump flow, the flow rate, the viscosity, or the threshold stress.

At step 200, the processing module 26 determines the last slump value $S_k$. The last slump value $S_k$ may correspond, for example, to the average of the latest slump values, for example the 5 last slump values, obtained at step 108. The method continues at step 202.

At step 202, the processing module 26 determines the difference Δs between a comparison slump value $S_e$ and the last slump value $S_k$. If the difference Δs is higher than a threshold TH, the method continues at step 204. If the difference Δs is lower than the threshold TH, the method returns to step 200. The threshold TH translates the accepted slump variation. Typically for a standard concrete, the threshold TH may be of the order of 30 mm.

At step 204, the processing module 26 determines the quantity of water (Addition) to be added. The Addition quantity may be determined by the following relationship (26):

$$\text{Addition} = Tx_{water} \cdot V \cdot \Delta S \cdot K_s \tag{26}$$

where $Tx_{water}$ corresponds to the quantity of water to be added by cubic meter of concrete and by millimeter of slump variation, $K_s$ is a safety coefficient and V is the volume of concrete. The quantity of water $Tx_{water}$ ranges, for example, between 0.1 L/m³/mm and 3 L/m³/mm and the safety coefficient $K_s$ ranges for example between 0 and 1. The method continues at step 206.

At step 206, the processing module 26 determines the total quantity of water added ($Water_{tot}$) to the concrete from the placing of the concrete in the container 12. The total quantity of added water $Water_{tot}$ corresponds to the sum of the successive additions already achieved since the placing of the concrete in the container 12, the water addition (Addition) calculated at the previous step and not yet achieved, and of the quantity of water initially introduced in the concrete before loading into the container. The total quantity of water ($Water_{tot}$) is compared with a maximum quantity of water (Max) able to enter into the composition of said concrete. If the quantity of water $Water_{tot}$ is strictly higher than Max, the method continues at step 208. If the quantity of water $Water_{tot}$ is lower than or equal to Max, the method continues at step 212.

At step 208, the processing module 26 sends an alarm, for example to the driver of the mixer truck, by means of the interface 28.

At step 212, the processing module 26 determines if the addition of the quantity of water (Addition) must be achieved automatically. If the quantity of water (Addition) must be added automatically, the method continues at step 214. If the quantity of water (Addition) must not be added automatically, the method continues at step 216.

At step 216, the processing module 26 waits for a manual validation to be achieved, for example, by the driver of the mixer truck, by means of the interface 28. When the manual validation is achieved, the method continues at step 214. If, at step 216, the manual validation is not achieved, the method returns to step 200.

At step 214, the quantity of water (Addition) is added into the container 12. This may be achieved by controlling the valve 40 by the processing module 26. The method continues at step 218.

At step 218, the method waits during a determined period, for example 5 minutes, for the added water to be appropriately mixed with the concrete, before returning to step 200.

The method may further, comprise the display on the display screen 28 of information pertaining to the concrete, the printing out of these information on a support or the storage of these information to a memory. These information may comprise the workability parameter determined at step 200, the quantity of water and/or adjuvant added to the concrete at step 214 or the formulation of the modified concrete after addition of the water and/or the adjuvant.

The control method according to the invention implemented by the processing module 26 may be achieved by material process, i.e. by a dedicated electronic circuit. By way of alternative, the control method according to the invention may be at least partially implemented by executing by the module 26 for processing instructions from a computer programme for example stored in the memory 27.

The control method according to the invention advantageously allows determining a workability parameter when the concrete is in the mixer with a non vertical rotational axis. It further, allows obtaining a measurement of the workability parameter which is more representative of the state of the concrete than the measurement which would be obtained based on a test implementing a sampling of a low volume of concrete with respect to the total volume contained in the mixer with a non vertical rotational axis.

Particular embodiment examples of the present invention have been described. Various alternatives and modifications will become apparent to the one skilled in the art. Particularly, even though the present invention has been described in the case where the motor torque is determined based on measurements of hydraulic pressure, it is clear that the present invention may be implemented in the case where the motor torque is measured directly by a torque sensor, comprising for example strain gauges. Furthermore, although the present invention has been described in the case of a mixer with a non vertical rotational axis of which the container is driven in rotation by a hydraulic motor, it may be implemented in the case where the container is driven in rotation by a thermal motor or by an electric motor by means of a speed reduction mechanical system. The motor torque may thus be measured by any suitable means. Particularly, when the container is driven in rotation by an electric motor, the motor torque may be determined based on a measurement of the supply current of the electric motor.

The invention claimed is:

1. A method for controlling at least one workability parameter of a concrete contained in a container of a mixer with a non vertical rotational axis, comprising:
   making the container turn at at least two different rotational speeds ω;
   determining, for each of said at least two rotational speeds ω, a rotary drive torque C of the container, a value of shear stress τ of the concrete and a value of speed gradient $\dot{\gamma}$ of the concrete according to the following relationships:

$\tau = T(\omega) \cdot C$ $\dot{\gamma} = G(\omega) \cdot \omega$ where T and G are predetermined functions;
   determining a relationship of variation of the shear stress τ according to the speed gradient $\dot{\gamma}$ by extrapolation and/or approximation based on the determined values; and
   providing an indication of the workability parameter of the concrete based on the relationship of variation, wherein the functions G and T are obtained by determining:

for each concrete of a plurality of different concretes, a variation curve of the drive torque of the container containing said concrete according to the rotational speed of the container;

for each concrete of a plurality of different concretes, a variation curve of the shear stress of the concrete according to the seed gradient of the concrete b means of a rheometer; and for each pair of concretes of the plurality of different concretes, a first point of intersection ($H_i$) between the variation curves of the drive torque of the container according to the rotational speed of the container for the concretes of the pair and a second point of intersection ($L_i$) between the variation curves of the shear stress according to the speed gradient for the concretes of the pair.

2. The method according to claim 1, comprising:

making the container turn at a first rotational speed and determining a first rotary drive torque of the container at the first rotational speed;

making the container turn at a second rotational speed and determining a second rotary drive torque of the container at the second rotational speed;

determining a first shear stress equal to the product of the first torque and to the value of the function T at the first rotational speed;

determining a first speed gradient equal to the product of the first rotational speed and to the value of the function G at the first rotational speed;

determining a second shear stress equal to the product of the second torque and to the value of the function T at the second rotational speed;

determining a second speed gradient equal to the product of the second rotational speed and to the value of the function G at the second rotational speed; and determining the relationship of variation of the shear stress according to the speed gradient by extrapolation and/or approximation based on the first and second shear stresses and the first and second speed gradients.

3. The method according to claim 2, comprising:

making the container turn at a third rotational speed and determining a third rotary drive torque of the container at the third rotational speed;

determining a third shear stress equal to the product of the third torque and to the value of the function T at the third rotational speed;

determining a third speed gradient equal to the product of the third rotational speed and to the value of the function G at the third rotational speed; and determining the relationship of variation of the shear stress according to the speed gradient by extrapolation and/or approximation in addition based on the third shear stress and the third speed gradient.

4. The method according to claim 1, wherein the workability parameter of the concrete is selected from the group consisting of the slump, the slump flow, the threshold stress, the viscosity and the flow rate.

5. The method according to claim 1, comprising determining a threshold stress of the concrete based on the relationship of variation and the determination of the slump and/or slump flow based on the threshold stress.

6. The method according to claim 1, comprising adjusting in the container the workability parameter of the concrete by introducing a compound into the container.

7. The method according to claim 6, wherein the compound comprises water, an adjuvant or a mixture thereof.

8. The method according to claim 1, wherein providing the indication of the workability parameter of the concrete includes displaying on a display screen the workability parameter, printing out of the workability parameter onto a support and/or storing a datum representing the workability parameter to a memory.

9. The method according to claim 1, wherein the container is driven in rotation by a hydraulic motor comprising an inlet for receiving a hydraulic fluid and an outlet for pushing back the hydraulic fluid, the torque being determined based on a first difference of pressures equal to the difference between the hydraulic pressure measured at the inlet of the hydraulic motor and the hydraulic pressure measured at the outlet of the hydraulic motor.

10. The method according to claim 9, wherein the first difference of pressures is decreased by a second difference of pressures equal to the difference between the hydraulic pressure at the inlet of the hydraulic motor and the hydraulic pressure at the outlet of the hydraulic pressure in the absence of concrete in the container at the measurement rotational speed.

11. The method according to claim 9, wherein the hydraulic pressure measured at the inlet or at the outlet of the hydraulic motor is equal to the average of a number of sampled pressure values, said number being inversely proportional to the rotational speed of the container.

12. The method according to claim 11, wherein during the sampling of the pressure values used for obtaining the hydraulic pressure measured at the inlet or at the outlet of the hydraulic motor, the variations of the rotational speed of the container are lower than a threshold.

13. The method according to claim 1, wherein for the first point of intersection ($H_i$) and the second point of intersection ($L_i$) of each pair of concretes of the plurality of different concretes, the method comprises determining the value $Gi^{CC}$ of the function G and the value $Ti^{CC}$ of the function T according to the following relationships:

$$G_i^{CC} = \frac{\dot{\gamma}_i}{\omega_i}$$

$$T_i^{CC} = \frac{\tau_i}{C_i}$$

where $\dot{\gamma}_i$ is the speed gradient at the second point of intersection, $\tau i$ is the shear stress of the concrete at the second point of intersection, $C_i$ is the drive torque at the first point of intersection and $\omega_i$ is the rotational speed at the first point of intersection.

14. The method according to claim 1, wherein for the first point of intersection ($H_i$) and the second point of intersection ($L_i$) of each pair of concretes of the plurality of different concretes, the method comprises determining a value $Gi^{Alt}$ of the function G and a value $Ti^{Alt}$ of the function T according to the following relationships:

$$G_i^{Alt} = \sqrt{\frac{C_i}{V \cdot \eta_i \cdot \omega_i}}$$

$$T_i^{Alt} = \frac{1}{G_i^{Alt} \cdot V}$$

where V is the volume of concrete in the container, is the apparent viscosity of the concrete equal to the ratio of the shear stress of the concrete at the second point of intersection ($L_i$) and the speed gradient at the second point of intersection, $C_i$ is the drive torque at the first point of intersection ($H_i$) and $\omega_i$ is the rotational speed at the first point of intersection.

15. A memory device on which is stored a computer program for implementing the method according to claim 1.

* * * * *